United States Patent
Causevic

(10) Patent No.: US 8,577,451 B2
(45) Date of Patent: Nov. 5, 2013

(54) SYSTEM AND METHODS FOR NEUROLOGIC MONITORING AND IMPROVING CLASSIFICATION AND TREATMENT OF NEUROLOGIC STATES

(75) Inventor: Elvir Causevic, Clayton, MO (US)

(73) Assignee: BrainScope Company, Inc., Bethesda, MD (US)

( * ) Notice: Subject to any disclaimer, the term of this patent is extended or adjusted under 35 U.S.C. 154(b) by 666 days.

(21) Appl. No.: 12/639,218

(22) Filed: Dec. 16, 2009

(65) Prior Publication Data

US 2011/0144519 A1    Jun. 16, 2011

(51) Int. Cl.
*A61B 5/04*    (2006.01)

(52) U.S. Cl.
USPC .......................................................... 600/544

(58) Field of Classification Search
USPC .......................................................... 600/544
See application file for complete search history.

(56) References Cited

U.S. PATENT DOCUMENTS

| | | | |
|---|---|---|---|
| 4,835,313 A * | 5/1989 | Pietruszkiewicz et al. ... | 564/225 |
| 4,928,704 A | 5/1990 | Hardt | |
| 5,189,018 A * | 2/1993 | Goldman et al. ............ | 514/10.8 |
| 6,622,036 B1 | 9/2003 | Suffin | |
| 6,866,639 B2 | 3/2005 | Causevic et al. | |
| 6,974,421 B1 | 12/2005 | Causevic et al. | |
| 7,054,453 B2 | 5/2006 | Causevic et al. | |
| 7,123,955 B1 | 10/2006 | Gao et al. | |
| 7,187,790 B2 | 3/2007 | Sabol et al. | |
| 7,256,708 B2 | 8/2007 | Rosenfeld et al. | |
| 7,321,862 B2 | 1/2008 | Rosenfeld et al. | |
| 7,490,085 B2 | 2/2009 | Walker et al. | |
| 2002/0091335 A1 | 7/2002 | John et al. | |
| 2002/0188217 A1 | 12/2002 | Farwell | |
| 2003/0135128 A1 | 7/2003 | Suffin et al. | |
| 2003/0139684 A1 | 7/2003 | Thornton | |
| 2003/0153818 A1* | 8/2003 | Bocionek et al. ............. | 600/300 |
| 2003/0225340 A1 | 12/2003 | Collura | |
| 2004/0015337 A1 | 1/2004 | Thomas et al. | |
| 2004/0122719 A1 | 6/2004 | Sabol et al. | |
| 2004/0122790 A1 | 6/2004 | Walker et al. | |
| 2004/0172305 A1 | 9/2004 | Soerensen | |
| 2006/0153396 A1 | 7/2006 | John | |
| 2006/0241697 A1 | 10/2006 | Libbus et al. | |
| 2007/0032737 A1 | 2/2007 | Causevic et al. | |
| 2007/0106169 A1 | 5/2007 | Fadem | |
| 2007/0118399 A1 | 5/2007 | Avinash et al. | |
| 2008/0004904 A1 | 1/2008 | Tran | |
| 2008/0125669 A1 | 5/2008 | Suffin | |

(Continued)

FOREIGN PATENT DOCUMENTS

EP    1 541 082 A1    6/2005
GB    2 437 106 A    10/2007

(Continued)

OTHER PUBLICATIONS

Co-Pending U.S. Appl. No. 12/615,423, filed Nov. 10, 2009.

(Continued)

*Primary Examiner* — Navin Natnithithadha
*Assistant Examiner* — Etsub Berhanu
(74) *Attorney, Agent, or Firm* — Finnegan, Henderson, Farabow, Garrett & Dunner, LLP

(57) ABSTRACT

Methods and systems for assessing brain activity and collecting information related to a patient's condition and brain electrical activity are provided.

14 Claims, 3 Drawing Sheets

(56) References Cited

U.S. PATENT DOCUMENTS

| | | |
|---|---|---|
| 2008/0208073 A1 | 8/2008 | Causevic |
| 2008/0228522 A1 | 9/2008 | Davis et al. |
| 2009/0105785 A1 | 4/2009 | Wei et al. |
| 2009/0137923 A1* | 5/2009 | Suffin et al. ............... 600/544 |
| 2009/0220429 A1 | 9/2009 | Johnsen et al. |
| 2009/0264785 A1 | 10/2009 | Causevic |

FOREIGN PATENT DOCUMENTS

| | | |
|---|---|---|
| WO | WO 00/16690 | 3/2000 |
| WO | WO 00/35344 | 6/2000 |
| WO | WO 02/098291 A2 | 12/2002 |
| WO | WO 2005/072459 A2 | 8/2005 |
| WO | WO 2005/072608 A1 | 8/2005 |
| WO | WO 2006/034024 A2 | 3/2006 |
| WO | WO 2007/140535 | 12/2007 |
| WO | WO 2008/148894 A1 | 12/2008 |
| WO | WO 2009/045449 A1 | 4/2009 |

OTHER PUBLICATIONS

Co-pending U.S. Appl. No. 12/638,602, filed Dec. 15, 2009.
PCT International Search Report and Written Opinion mailed Jan. 28, 2011, in PCT/US2010/055954.
PCT International Search Report and Written Opinion mailed Mar. 25, 2011, in PCT/US2010/060182.
PCT International Search Report and Written Opinion mailed Mar. 3, 2011, in PCT/US2010/059836.

* cited by examiner

SYSTEM AND METHODS FOR NEUROLOGIC MONITORING AND IMPROVING CLASSIFICATION AND TREATMENT OF NEUROLOGIC STATES

The present disclosure pertains to devices and methods for monitoring and evaluating patients, and more specifically, to monitoring and evaluating neurologic conditions.

There are many medical and surgical situations that require prompt and accurate diagnosis or triage to ensure optimum outcomes. However, it is often difficult to get a patient to a hospital or other site that has the most up-to-date diagnostic resources, and/or has staff available for accurate and rapid patient assessment. Further, as new medical information is generated through the experience of health care professionals at different locations, there can be significant time lags before such information is disseminated to other professionals or incorporated into technology that helps implement diagnosis or therapy. In addition, improved systems for documenting the neurologic condition of a patient over time and using the documented information to guide patient evaluation and treatment are needed.

It is accordingly an object of the systems and methods of the present disclosure to provide tools for assessing patients and updating databases using data collected at various locations to improve diagnostic accuracy and specificity.

SUMMARY

A method for monitoring or evaluating a neurologic state of a patient is provided. The method comprises collecting data related to brain electrical activity of a patient at a first location; transferring the data related to brain electrical activity to a memory unit located at a second location that is different from the first location; providing a classification of at least one neurological state of the patient based on the data related to brain electrical activity and data stored in a database; receiving information related to the at least one neurological state of the patient based on at least one evaluation technique not including brain electrical activity data; and updating the database to include the data related to brain electrical activity and the information related to the neurological state.

A system for monitoring or evaluating a neurologic state of a patient is provided. The system comprises a sensing device including at least one electrode configured to detect a brain electrical signal; a first processor configured to convert the electrical signal into data related to brain electrical activity of a patient at a first location; and a communication system configured to transfer the data related to brain electrical activity to a memory unit at a second location that is different from the first location and store the data in a first record in the memory unit; a second processor circuit configured to provide a classification of a neurological state of the patient based on the data related to brain electrical activity and data stored in a database; and a data entry interface configured to receive information related to the neurological state of the patient based on at least one evaluation technique not including brain electrical activity data and including a communication system configured to transfer the information related to the neurological state of the patient to the database.

A method for monitoring or evaluating a neurologic state of a patient is provided. The method includes collecting data related to brain electrical activity of a patient at a first location; transferring the data related to brain electrical activity to a memory unit located at a second location that is different from the first location; providing a classification of at least one neurological state of the patient based on the data related to brain electrical activity and data stored in a first database; updating the database to include the data related to brain electrical activity and the information related to the neurological state; and updating a second database containing information related to the patient's neurologic state at multiple times points.

A method for monitoring or evaluating a neurologic state of a patient is provided. The method can include collecting data related to brain electrical activity of a patient at a first location; transferring the data related to brain electrical activity to a memory unit located at a second location that is different from the first location; providing a classification of at least one neurological state of the patient based on similarities in the data related to brain electrical activity and brain electrical activity data stored in a database for at least one additional patient; and providing a treatment recommendation based on the response of the at least one additional patient to said treatment.

DESCRIPTION OF EXEMPLARY EMBODIMENTS

Figure 1:
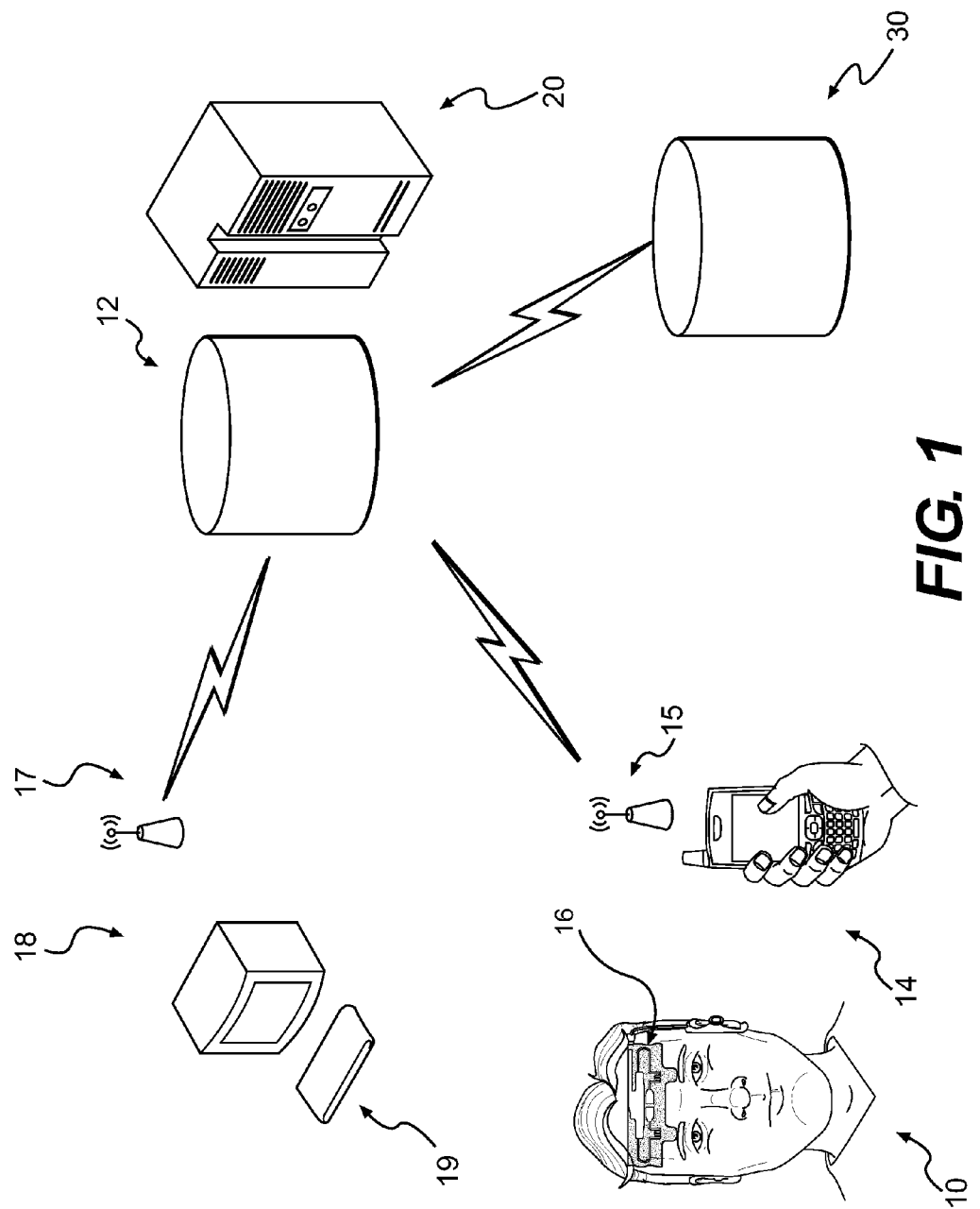
FIG. 1 illustrates a system for evaluating a neurologic state of a patient, according to certain embodiments of the present disclosure.

The present disclosure provides systems and methods for evaluating brain electrical activity and providing an assessment of a patient's neurological state based on the evaluation of the patient's brain electrical activity. In some embodiments, the assessment can be based on information contained in a database including numerous brain electrical activity data sets, including, for example, features related to normal brain state and/or a variety of different diseases, pathologies or injury states. In some embodiments, the systems and methods of the present disclosure provide tools for assessing a patient's neurological state based on a database containing brain electrical activity data for numerous patients, as well as methods and systems for verifying the assessment, updating the database to expand the data included therein, and/or improving the range of diseases or conditions that may be identified, and/or improving diagnostic sensitivity and/or specificity using the database.

In some embodiments, the systems and methods provide a self-updating database to automatically correlate, over time, brain electrical activity recordings with other non-electrical diagnostic information to allow automatic development of diagnostic and treatment algorithms. As described further below, the systems and methods can include a sensor and processor at a first location to collect data related to a patient's brain electrical activity. The data can be transferred to a centralized database, which may be at a different location than the data collection site. The centralized database can be updated with data at multiple time points and/or from multiple patients to allow automatic generation of diagnostic and treatment algorithms. In addition, the data can be stored in a second database, which includes longitudinal data from a specific patient, thereby allowing continuous monitoring of that patient's neurological status and/or providing ongoing treatment guidance.

The systems and methods can also facilitate treatment planning and decision-making. In some embodiments, the systems and methods provide a database of treatments administered to patients along with the effects of the treatments on electrical activity and/or other assessments of neurological status. Evaluation of the effects of treatments on patients with various brain electrical activity data classifications allows identification of improved or new treatment modalities. In some embodiments, the systems and methods provide a treatment suggestion system for patients whose symptoms, brain electrical activity, and/or other neurological assessments most closely approximate those of other patients previously stored in the database. The systems may further make a prediction for which treatment course would be best suited for a particular diagnostic assessment, including, for example, treatment types to avoid as prior database information shows lack of efficacy or deterioration in patient state due to the treatment.

As used herein, "brain electrical activity" will be understood to refer to any measurable electrical activity from the central nervous system, including electrical activity detected by any means, including for example, electroencephalography, and/or brainstem or other auditory, visual, or other sensory/somatosensory evoked responses.

FIG. 1 illustrates a system for evaluating a neurologic state of a patient, according to certain embodiments of the present disclosure. In some embodiments, the system includes an analysis system 10 for evaluating a neurologic state of a patient. The system can include a sensing device 16 including at least one electrode configured to detect a neurologic electrical signal. The system 10 can further include a first processor 14 configured to convert the electrical signal into data related to brain electrical activity of at least one patient at a first location; and a communication system 15 configured to transfer the data related to brain electrical activity to a memory unit 12 at a second location that is different from the first location and store the data in a first record in the memory unit 12. In addition, in some embodiments, processor 14 may be configured to analyze the data related to brain electrical activity and to provide an assessment of a neurological state of the patient based on the electrical activity. In other embodiments, the system 10 can include a second processor circuit 20 that performs the analysis of the brain electrical activity in addition to or in place of the analysis performed by processor 14.

The system can include data entry systems 18 that are able to receive information related to the neurological state of a patient that is based on an evaluation technique other than the classification based on brain electrical activity data. In some embodiments, the data entry systems 18 are configured to receive information related to an evaluation technique not including evaluation of brain electrical activity data. In addition, in some embodiments, the systems and methods of the present disclosure can include a data entry interface 19 configured to receive information related to the neurological state of a patient based on at least one evaluation technique not including brain electrical activity data. In addition, the system can further include a communication system 17 configured to transfer the information related to the neurological state of the patient to the memory unit 12 and processor 20.

The information related to the neurological state of a patient based on at least one evaluation technique not including brain electrical activity data can include a number of different data types. For example, the information can be derived from brain or neurological imaging studies such as CT scans, MRI, PET, angiograms, or any other suitable radiologic or imaging study that provides information related to brain structure and/or function. In addition, the information can be derived from various laboratory tests, which may be indicative of certain neurologic abnormalities. For example, suitable tests can include analyses of cerebrospinal fluid for substances indicative of infection, immunologic disorders, cerebral hemorrhage, or other neurologic processes. In addition, laboratory tests indicative of neurologic processes such as stroke, autoimmune disorders, medical or metabolic abnormalities that may affect neurologic function, presence of drugs or other substances in the blood. In some embodiments, the information can include an assessment made by a physician or other healthcare provider, including, for example, information related to physical examination or an overall assessment, differential diagnosis, or probable diagnosis based on examination and laboratory and imagining studies. The information can also include a neurologic cognitive exam based on question posed to test various neurocognitive abilities (e.g., memory, linguistic skills, or reasoning).

In various embodiments, the system 10 is configured to store information related to the brain electrical activity of a patient and information related to the neurological state of the patient based on at least one evaluation technique not including brain electrical activity data in memory units 12, 30. In some embodiments, memory units 12, 30 can include one or more databases containing data related to brain electrical activity. In certain embodiments, the system can include two or more databases. One database can be used to facilitate automatic algorithm development to assist in diagnosis and treatment by collecting data related to numerous different patients from, potentially, multiple locations. Other databases can store data related to a specific patient to allow longitudinal assessment and treatment of that patient.

In various embodiments, the information stored in units 12, 30 not including brain electrical activity data can be associated with the data related to brain electrical activity. Processors 20 and/or 14 can further be configured to produce a suspected diagnosis or patient neurological state/classification based on data previously stored in memory unit 12, and the diagnosis is compared to data not including brain electrical activity. In this way, the database can be updated automatically to become more sensitive and specific with subsequent diagnoses.

In order to associate the data associated with brain electrical activity with the data not including brain electrical activity, a record identifier may be assigned to the patient data. The record identifier can correspond to patient data taken from a particular patient and during a specified time period. Further, the same record identifier can be associated with data not related to brain electrical activity, and such record identifier can be used when inputting or transmitting data via interface 18.

In order to ensure patient confidentiality while allowing data in memory unit 12 to be updated and improved, various safe guard measures may be used. In some embodiments, the analysis system 10 is configured to transfer to the memory unit 12 the record identifier and not other information related to the identity of the patient other than the data related to brain electrical activity. In addition, the one or more additional memory units 30 can be configured to store the record identifier and information identifying the patient in a second record so that a person accessing the data in memory unit 12 cannot identify a particular patient associated with a certain neurological state or diagnosis. The additional memory units 30 may include hospital electronic record systems where a patient is being treated, and therefore, information that reveals the identity of the patient will only be available through traditional medical records that are accessible only by health care providers who have a need to know such information. In addition, in some embodiments, additional memory units 30 can be contained within the same structure or near processor 14 to allow continuous assessment and storage of data from a specific patient being evaluated or treated.

In addition, in order to allow the data in memory unit 12 to be valuable and free of user bias, the sources of information related to the neurological state of the patient based on at least one evaluation technique not including brain electrical activity data should not be influenced by a diagnosis provided through processor 14 or 20 based on data related to brain electrical activity. In some embodiments, the data entry interface 18 is configured to confirm that a person attempting to access the second memory unit (which contains information identifying a patient) has not accessed the assessment based on the data related to brain electrical activity, and not allow the person to access the second record if the person has accessed the assessment. In some embodiments, to confirm that the person attempting to access the second record has not accessed the classification, the person attempting to access the second record will be identified and permitted to access the second record only if the person is included in a predetermined group of people who are designated as being allowed to access the information. In other embodiments, the system will not allow the assessment of brain electrical activity to be accessed until a later time, e.g., after a definitive diagnosis is made by imaging or lab studies, or after a certain number of patients have been evaluated. In addition, in order to ensure that the sources of information related to the neurological state of the patient based on at least one evaluation technique not including brain electrical activity are not influenced by an assessment produced based on brain electrical activity, in some embodiments, only designated persons who do not have access to brain electrical activity will be permitted to enter information or patient assessments into the system based on information not including brain electrical activity.

It may be desirable to collect information related to patients' neurological states and to assist in providing neurological diagnoses at multiple different locations. For example, multiple healthcare facilities may wish to use the neurological diagnosis capabilities provided by the database within memory unit 12. In addition, in order to increase the number of patients within the stored dataset in memory unit 12, multiple patient evaluation sites may be used. Accordingly, in some embodiments the system includes two or more sensing devices located at two or more different locations, and/or two or more data entry interfaces located at two or more different locations.

As noted above, processor 14 may be configured to provide an assessment of a patient's neurological state based on brain electrical activity. However, it may be necessary to have a patient consent to the use of that information to update a database or dataset used for future patient assessment. Accordingly, in some embodiments, data collected at analysis unit 10 may be stored at the first location and used only for initial patient assessment and treatment until a patient or other competent person is able to consent to use of the data for a desired purpose other than patient treatment.

Figure 2:
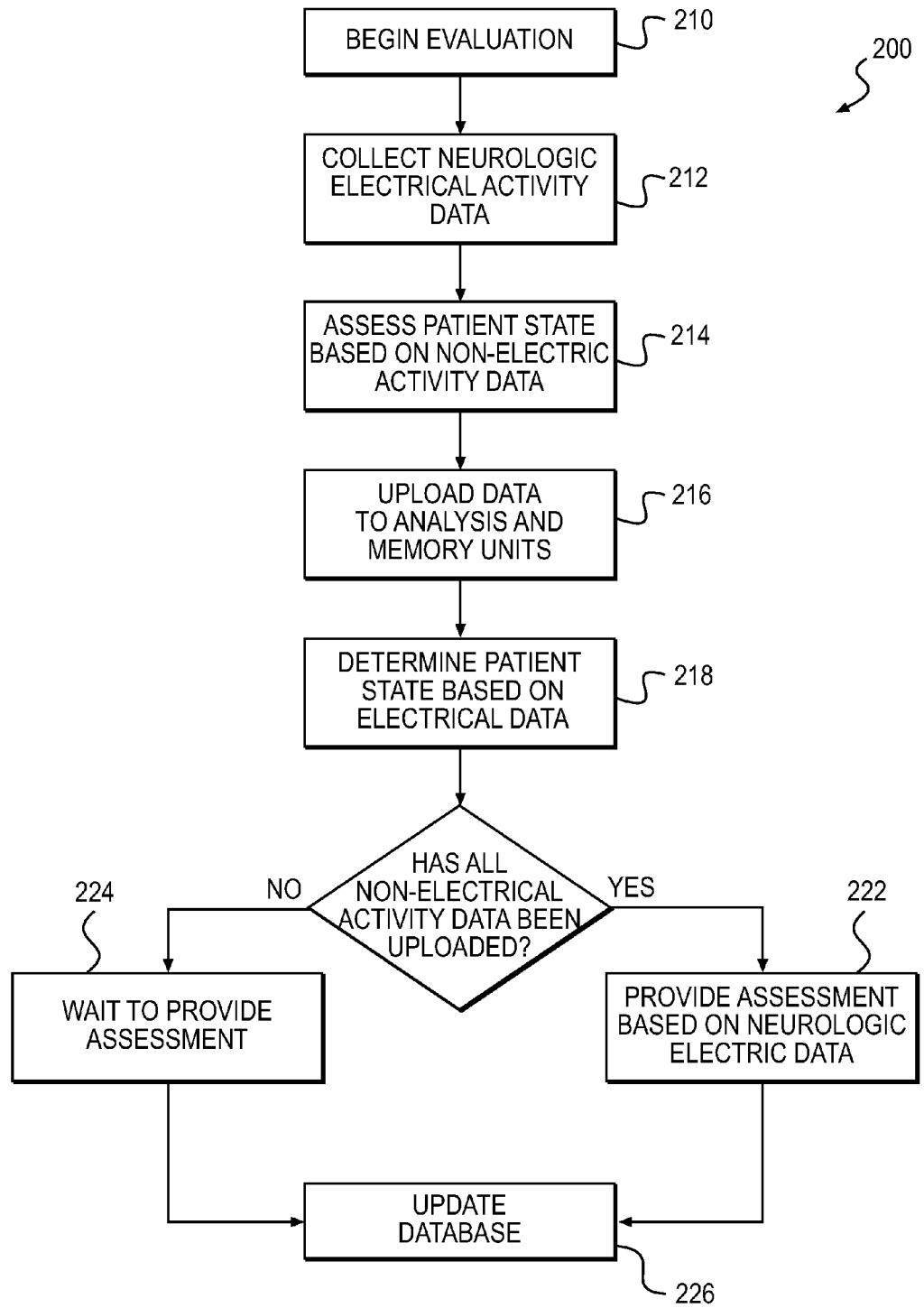
FIG. 2 illustrates a method for evaluating a neurologic state of a patient and updating a database for neurologic assessment, according to certain embodiments of the present disclosure.

FIG. 2 illustrates a method 200 for evaluating a neurologic state of a patient and updating a database for neurologic assessment, according to certain embodiments of the present disclosure. As shown at Step 210, the evaluation of a patient begins when a patient is identified as having a neurological state that should be screened or evaluated for abnormalities. This process can begin in a designated healthcare facility, e.g., hospital or trauma unit, or in a variety of different locations such as a battlefield, in an ambulance, in a primary care setting or other physician's office, or on a sports field.

After identification of a patient, data related to brain electrical activity of the patient is collected at a first location using, electrode 16 and processor 14, as shown at Step 212. Next, as shown at Step 214, the patient is assessed based on at least one evaluation technique not including brain electrical activity data, as described previously. Then, as shown at Step 216, the data related to brain electrical activity, and the data related to the neurological state of the patient not including brain electrical activity are transferred to processor 20 and memory unit 12 to update the database to include the data related to brain electrical activity and the information related to the neurological state.

At any time after collection of data related to brain electrical activity, an assessment of the patient's neurological state based on that activity can be made, as shown at Step 218. In some embodiments, processor 14 contains sufficient processing capabilities and data to allow an assessment to be made. In other embodiments, processor 14 is configured to transfer the data related to brain electrical activity to memory unit 12 located at a second location that is different from the first location, and the assessment is made at the second location.

The assessment of the patient's neurological state can be made based on a number of different factors. For example, in some embodiments, a patient's neurological state can be classified by comparing the data related to a patient's brain electrical activity to data stored in a database. In some embodiments, the classification can include identifying at least one similarity between the brain electrical activity data of the patient and brain electrical activity data stored in a database for at least one additional patient having a known neurological state and assigning the known neurological state to the patient. In some embodiments, the similarity can be between one or more signal features in the brain electrical activity data of the patient and brain electrical activity data stored in the database for at least one additional patient having a known neurological state, as described further below. In some embodiments, the at least one additional patient can include a group a patients. In other embodiments, the classification can be based on a comparison with data from the entire population of data present in the database. In certain embodiments, the classification can be based on a similarity in one or more neuromarkers, as described in detail in copending U.S. application Ser. No. 12/615,423, which is herein incorporated by reference in its entirety.

When the assessment is made at the data collection site using processor 14, it may be desirable to update processor 14 with information collected and stored within memory unit 12 from one or more different locations. Accordingly, processor 14 may be updated with a more recent dataset for use in patient assessment on a periodic basis. In this way, the quality of patient assessment using data related to brain electrical activity will be improved. When the patient assessment based on brain electrical activity is made using processor 12 and data stored in memory unit 20, such information can similarly be updated as new patient data is collected from various locations.

As noted above, the assessment can be related to a variety of different neurological states. Such states can include, for example, a normal brain state, a psychiatric disorder, an organic neurological disorder, a structural neurological disorder, a metabolic disorder, and/or intoxicated state. In some embodiments, the state includes an ischemic brain state, a hemorrhagic state, and/or an abnormal intracranial pressure.

In some embodiments, the person collecting information related to a patient's state and not including brain electrical activity will wish to receive the analysis based on brain electrical activity. However, in order to prevent the person making an assessment based on non-electrical data from being biased by the assessment based on brain electrical activity, the system 10 may be configured to confirm that all data based on non-electrical assessment has been uploaded before providing an assessment to the person.

After data based on neurologic electrical activity and non-electrical activity has been collected, such information can be used to update a database contained in memory unit 12. For example, in some embodiments, an assessment based on non-electrical activity is correlated with an assessment based on brain electrical activity, and differences between the assessments are used to automatically increase the sensitivity and specificity of the assessment based on brain electrical activity.

As noted above, the automatically updating database can be used to provide improved diagnostic accuracy and/or to facilitate treatment planning or guidance. Accordingly, in some embodiments, the systems and methods can be configured to store details related to specific treatments (e.g., drugs, surgeries, interventional procedures), which can be used to guide treatment planning. In addition, the systems can be configured to correlate patient responses to various treatments over time to assist in future treatment planning.

In addition, as noted above, the systems and methods can facilitate monitoring and treatment of specific patients over time. Accordingly, the system can be configured to store a detailed treatment record along with brain electrical activity data and other neurologic assessments. The treatment record and data related to the patient's neurologic state can be compared to other patients within a centralized database, and based on the comparison, future treatment recommendations can be made. In addition, the response of the patient to that treatment or lack thereof can be used to update the database.

Figure 3:
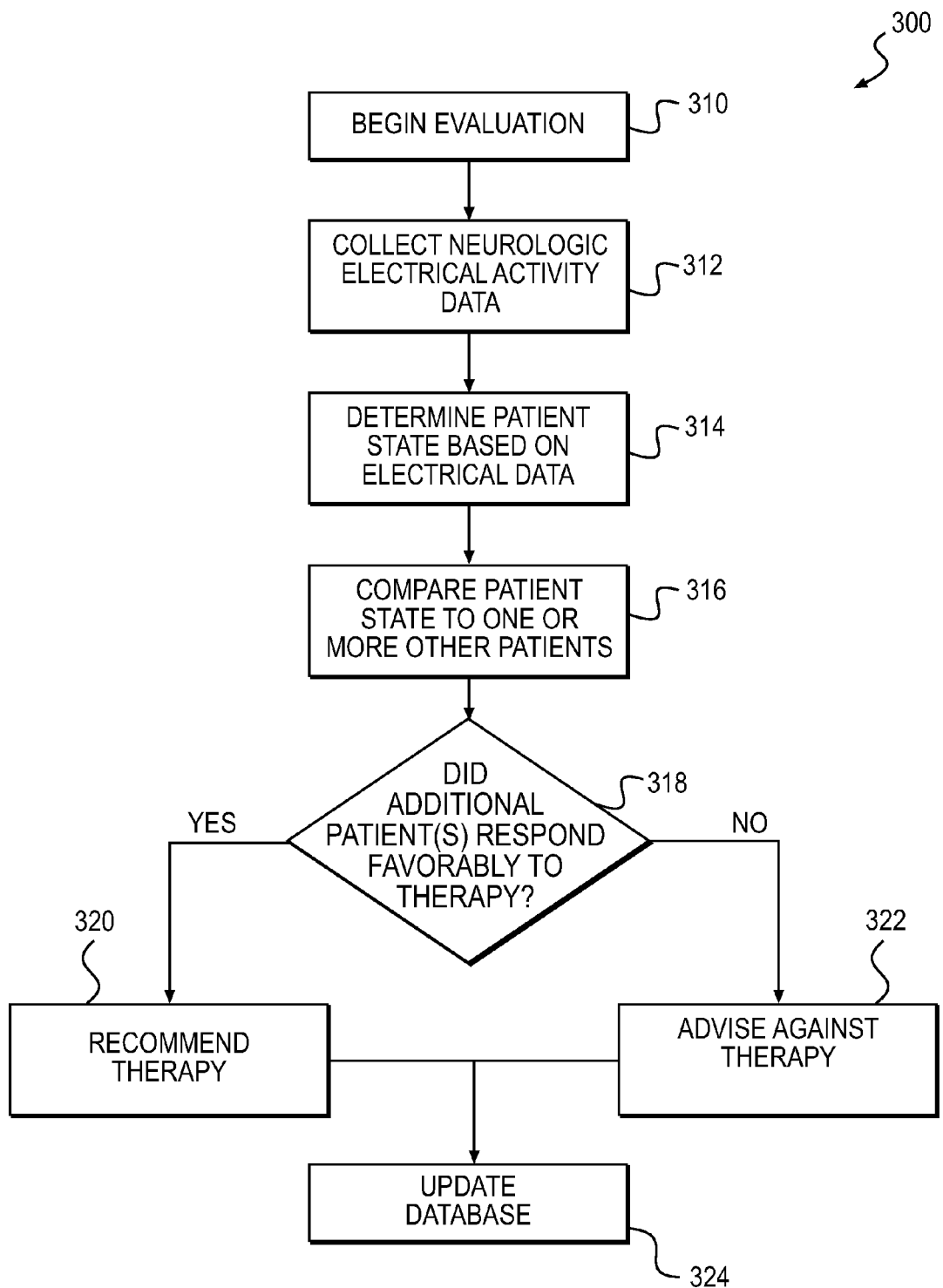
FIG. 3 illustrates a method for evaluating a neurologic state of a patient and providing a treatment recommendation based on the evaluation, according to certain embodiments of the present disclosure.

FIG. 3 illustrates a method 300 for evaluating a neurologic state of a patient and providing a treatment recommendation based on the evaluation, according to certain embodiments of the present disclosure. As shown at Step 310, the evaluation of a patient begins when a patient is identified as having a neurological state that should be screened or evaluated for abnormalities.

After identification of a patient, data related to brain electrical activity of the patient is collected at a first location using electrode 16 and processor 14, as shown at Step 312. Next, after collection of data related to brain electrical activity, an assessment of the patient's neurological state based on that activity can be made, as shown at Step 314. In some embodiments, processor 14 contains sufficient processing capabilities and data to allow an assessment to be made. In other embodiments, processor 14 is configured to transfer the data related to brain electrical activity to memory unit 12 located at a second location that is different from the first location, and the assessment is made at the second location.

As described with reference to FIG. 2, the assessment of the patient's neurological state can be made based on a number of different factors. For example, in some embodiments, a patient's neurological state can be classified by comparing the data related to a patient's brain electrical activity to data stored in a database. In some embodiments, the classification can include identifying at least one similarity between the brain electrical activity data of the patient and brain electrical activity data stored in a database for at least one additional patient having a known neurological state and assigning the known neurological state to the patient. In some embodiments, the similarity can be between one or more signal features in the brain electrical activity data of the patient and brain electrical activity data stored in the database for at least one additional patient having a known neurological state, as described further below. In some embodiments, the at least one additional patient can include a group a patients. In other embodiments, the classification can be based on a comparison with data from the entire population of data present in the database. In certain embodiments, the classification can include a similarity in one or more neuromarkers, as described in detail in copending U.S. application Ser. No. 12/615,423, which is herein incorporated by reference in its entirety.

Next, in order to guide treatment, the patient's neurological state can be compared to that of one or more additional patients represented in a database, as shown at Step 316. In some embodiments, based on the comparison, one or more patients having similarities in brain electrical activity are identified, and the therapies provided to the patient(s) are evaluated, as shown at Step 318. Further, if the one or more additional patients were known to have a positive response (e.g., improvement in electrical activity or other measure of function) to one or more therapies, then the system may recommend the one or more therapies, as shown at Step 320. Alternatively, if the patient had a negative response to one or more therapies, the system may advise against the therapies, as shown at Step 322.

In addition, the patient's response to recommended or discouraged therapies can be used to update the database, as shown at Step 324. In this way, the system provides a method for automatic improvement in treatment planning. Further, other therapies provided to the patient can be used to update the database. Specifically, in some embodiments, a detailed log of therapies provided to the patient can be stored and used to update the database as the patient's condition is periodically or continually assessed.

Signal Pre-Processing

As described above, classification of a patient's neurological state can be based on a comparison between one or more signal features in the patient's brain electrical activity. Prior to signal processing, one or more pre-processing steps may be applied to the brain electrical signal. For example, a brain electrical signal may require denoising, filtering, windowing, sampling, or digitizing. In particular, artifact identification and removal may use a signal processing method as described in commonly-assigned U.S. patent application Ser. No. 12/106,699, which is incorporated herein by reference in its entirety. Artifact identification and rejection can require transforming a signal into one or more components, computing their fractal dimension, identifying noise components based on their fractal dimension, attenuating the identified noise components, or reconstructing a denoised signal using inverse transform.

Initially, a brain electrical signal can be digitized and then deconstructed into constitutive coefficients using a linear or non-linear transformation method, such as, a Fast Fourier Transform (FFT), an Independent Component Analysis (ICA) transform, a wavelet transform, or a wavelet packet transform. Suitable methods are described in commonly assigned U.S. patent application Ser. No. 11/195,001 titled "Method For Assessing Brain Function and Portable Automatic Brain Function Assessment Apparatus," U.S. patent application Ser. No. 12/041,106 titled "Field-Deployable Concussion Detector," and U.S. patent application Ser. No. 12/106,657 titled "System and Method For Signal Denoising Using Independent Component Analysis and Fractal Dimension Estimation," each of which are incorporated herein by reference in their entirety. The fractal dimensions of the coefficients can then be calculated in the transform domain, and the coefficients that have fractal dimensions higher than a threshold value attenuated. The intact and re-scaled coefficients can then be remixed using an inverse transform to generate a denoised signal. Such a signal can then be further processed to extract features and classify the extracted features, as described in detail below.

In some embodiments, a wavelet transformation can be used to perform an signal denoising operation prior to a feature extraction. Optional denoising can use wavelet coefficient thresholding to separate incoherent noise from the coherent signals. Specifically, a wavelet transform can be performed on a brain electrical signal to obtain a number of wavelet coefficients at different scales. Threshold levels can be set for various noise components, and any coefficient below these thresholds can be set to zero or reduced. As such, wavelet transformation of brain electrical signals can provide fast and efficient denoising for rapid feedback while monitoring a patient's brain activity. Wavelet transformations do not generally require heavy computational demands, or large amounts of computer memory, and can facilitate application in small, portable devices.

In operation, the wavelet transform can include an integral transform that projects the original brain electrical signal onto a set of unconditional basis functions called wavelets. The transformation can use a discrete waveform, an orthogonal wavelet, a bi-orthogonal wavelet, or some wavelets may be continuous. Also, the wavelet transform can be used to obtain a number of wavelet coefficients at different scales. In some embodiments, a series of different wavelets may be used for denoising, feature extraction, or other signal processing.

Many types of wavelets which may be used to develop a wavelet transform, and various types of wavelet transforms exist. Various other de-noising algorithms and data removal techniques may also be employed. For example, suitable denoising techniques are described in U.S. Pat. Nos. 7,054,453, 7,054,454, 7,302,064, 7,333,619, and International Publication No. WO 2006/034024, each of which are incorporated herein by reference in their entirety.

Signal Feature

As described above, assessment of a patient's neurological state can include comparison of one or more signal features of a patient's brain electrical activity data with signal features of one or more additional patients. A signal feature can include any readily identifiable component, or processed component, associated with a signal representative of neuronal activity. For example, a feature could include an amplitude, frequency, period, phase, real or imaginary component of a brain electrical signal recorded from the skull of a patient. Additionally, a signal feature could include a statistical parameter associated with a signal associated with brain activity, such as, for example, an average, mean, standard deviation, or other statistical measure of one or more signals. Other statistical methods can include t-test, chi-square, ANOVA, regression analysis, factor analysis, and time series analysis. In some instances, a feature can include a quantifiable measure of a signal associated with brain activity. Any signal feature, or representation of a feature, could be stored in a database for later use, as described in detail below.

In some embodiments, a feature could be derived from a brain electrical signal. For example, a signal feature could be derived by integrating, differentiating, or applying a mathematical function to a brain electrical signal. Such processing can be used to determine an area under a brain electrical signal, a gradient of a brain electrical waveform, or other parameter associated with the brain electrical signal. For example, a Fourier transform (FT) could be applied to a brain electrical signal. Based on FT processing, a feature could include a real or complex number, time, frequency, vector, matrix, harmonic, z-score, eigenvalue, or other parameter derived from FT processing.

In other embodiments, a signal feature could include a parameter derived from the application of one or more algorithms. For example, a feature could include a variable associated with linear or non-linear processing of a brain electrical signal. In particular, a feature could be derived from the application of wavelet, wavelet-packet, diffusion wavelet, or fractal mathematics techniques. Also, a signal feature could include a waveform, cloud, cluster, or other representation associated with non-linear processing of a brain electrical signal. In addition, a signal feature could further be associated with a partition of data, subset of data, or combination of multiple data.

Signal Feature Extraction

In some embodiments, a feature can be extracted from a brain signal, before, after, or during a processing step. For example, a signal feature could include a variable associated with an unprocessed signal, obtained before a brain electrical signal is processed. Such "raw" features could be extracted from Delta, Theta, Alpha, Beta, Gamma, or high frequency bands. Signal features could also be extracted via a processing step. For example, data from a brain electrical signal could be removed by a processing step, and the removed data could be used, or further processed, as a feature. Also, filtered, sub-threshold, noise, or other data could be used to extract a feature.

In certain instances, a feature could also be extracted following brain electrical signal processing. As previously described, various filters, algorithms, or other data processing techniques can be applied to a brain electrical signal. Following, various processed data are available for further analysis. Such processed data may also be used to determine a signal feature as described above for a feature associated with an unprocessed brain electrical signal. For example, a feature could include the amplitude of a waveform created by processing a brain electrical signal using a wavelet analysis technique. Another signal feature could be based on spectral analysis of such a waveform, or additional processing of a previously processed signal.

A signal feature can be analyzed using various mathematical methods. For example, multiple signal features could be subject to statistical measures to determine average, standard deviation, and other statistical measures, as outlined above. The signal feature could be derived from a single brain electrical signal or a combination of brain electrical signals. Further, a spatial collection or time series of features could be analyzed. For example, a feature could be obtained from a brain electrical signal obtained from only the left hemisphere of the brain, only the right hemisphere, or from two signals from both hemispheres. A feature could also be extracted from brain electrical signals obtained at different times. For example, brain electrical signals obtained before and after a stimulus has been applied to a patient may be used to determine a feature.

In some instances, a signal feature can be extracted following data removal from a brain electrical signal, while in other instances a "raw" brain electrical signal can used. As described in more detail below, linear or non-linear signal processing techniques can be used to extract a feature. Such techniques can include, for example, the use of wavelet-packets, diffusion wavelet processing, or fractal mathematics. For example, suitable wavelet-packet techniques are well known. In addition, suitable diffusion wavelet techniques are described in commonly-assigned U.S. patent application Ser. No. 12/105,439 titled "Method and Apparatus for Assessing Brain Function Using Diffusion Geometric Analysis." Suitable fractal mathematics techniques are described in commonly-assigned U.S. patent application Ser. Nos. 12/106,699 and 12/106,657, titled respectively "System and Method for Signal Processing Using Fractal Dimension Analysis" and "System and Method for Signal Denoising Using Independent Component Analysis and Fractal Dimension Estimation." In addition, other advanced processing techniques may be employed, as described, for example, in commonly-assigned U.S. Patent Application Publication No. 2007/0032737A1. Each of these above references are incorporated herein by reference in their entirety In some embodiments, brain electrical signal processing can include extracting one or more features from a denoised brain electrical signal. For example, a feature extraction algorithm can be configured to perform a linear feature extraction algorithm based on FFT and power spectral analysis, according to a method disclosed in commonly-assigned U.S. Patent Application Publication No. 2007/032737, and U.S. patent application Ser. No. 12/041,106, both of which are incorporated herein by reference in their entirety.

A linear algorithm could be configured to extract a feature by Fourier transforming a frequency band and calculating the power of the frequency band. The frequency composition can be analyzed by dividing the signal into Delta, Theta, Alpha, Beta, or Gamma bands as previously described. In some instances, higher frequencies up to and beyond 1000 Hz may also be used. A univariate signal feature can then be determined by calculating the absolute and relative power for each electrode or between a pair of electrodes within a select frequency band. Following, an asymmetry and coherence relationship among the spectral measurements can be determined. In some instances, multivariate features derived from non-linear functions of univariate features may also be used. Such measures can be age-regression normalized, or Z-transformed to extract features (Z-scores) for discriminant analysis.

In another embodiment, a linear feature extraction algorithm can be based on wavelet transforms, such as Discrete Wavelet Transform (DWT), Continuous wavelet transform, or Complex Wavelet Transforms (CWT). Although Fourier analysis often provides a less computationally demanding method of signal processing and feature selection, transitory information can be lost in the frequency domain. FFT-based spectral estimation assumes a stationary and slowly varying signal, however brain electrical signals can be time-varying, transient (e.g. spikes/bursts), or non-stationary. Fourier transforms can provide rhythmic frequency information, but may not reveal temporal frequency data. If time localization of a spectral component is required, a transform should provide a time-frequency information. Wavelet analyses are well-suited for such application because of their high time-frequency resolution and low computational complexity.

In some embodiments, signal feature extraction can use a non-linear signal transform method, such as a wavelet packet transform. Such a transform can extract a Local Discriminant Basis (LDB) feature, wherein a LDB algorithm can define a set of features that are optimized for statistical discrimination between different classes of signals. These signal features are initially calculated using power spectral densities over a set of epochs associated with each electrode channel. For each patient, the algorithm produces one power spectrum per channel, and then power spectra quotients for each pair of channels are calculated. For example, a five channel system produces fifteen power spectra per subject, permitting calculation of fifteen distinct bases, or sets of LDB vectors. An LDB feature can then be determined using a wavelet packet table for each power spectrum and a Haar or other standard or custom wavelet function. The function can be applied to low and high pass sub-bands, generating a tree structure of possible wavelet packet bases. Accordingly, signals can then be decomposed into a time-frequency dictionary.

In another embodiment consistent with the present disclosure, diffusion geometric analysis can be used to extract a non-linear feature according to a method disclosed in commonly-assigned U.S. patent application Ser. No. 12/105,439, which is incorporated herein by reference in its entirety. Initially, brain electrical data set can be organized into a plurality of digital documents, each document including a time window of temporal information associated with each electrode. Affinity between the documents may then be computed using an appropriate affinity matrix A. The affinity matrix A, between a document at time i and a document at time j may be defined as:

$$A_{i,j} = \frac{e^{\frac{-\|v(i)-v(j)\|^2}{\varepsilon}}}{w(i)w(j)}$$

wherein $\varepsilon$ is a threshold parameter, $w(i)$ is a weighting function at time i, $w(j)$ is the weighting function at time j, and the weighting functions are selected such that A is Markov in i and j. Next, the eigenvectors of the affinity matrix can be determined and used to construct a Euclidean space representing the diffusion geometry of the dataset including a plurality of diffusion coordinates. If the first three eigenvectors are used, an embedding in three dimensional Euclidean space can be obtained wherein the diffusion metric, or relational inference, can be isometrically converted to a corresponding Euclidean distance. A feature may be obtained based on the metrics provided by the diffusion geometry analysis.

Feature Library

A feature may be determined based on various criteria. For example, a predetermined portion of the diffusion coordinates space may be partitioned into data corresponding to a particular feature. In another embodiment, applying diffusion geometric analysis to multiple digital documents may result in a formation in multi-dimensional space, such as, for example, a cluster. The cluster could be initialized based on one metric, and then hierarchically aggregated based on a different metric from the multiplicity of metrics corresponding to the diffusion distances. Such a cluster may represent a specific feature, part of a feature, or set of features, depending on the metrics used to initialize the cluster.

An association between a signal feature and brain state can include a statistical association, a correlation, a comparison, or similar relationship. For example, one or more features could be associated with a disease state by gathering signal data for many patients with a known disease. The patient population data may be processed using the non-linear methods described herein. Statistical analysis of this processed data could then be used to identify one or more features that indicate a particular disease state. In other instances, correlative techniques could be used wherein the features of two or more disease states are correlated. Such a correlation may permit prognostic evaluation of a patient without having obtained features specific for the patient's particular disease state. Feature comparison could also be used to determine an association. For example, a feature could be associated with blood pressure and a certain disease could be known to affect blood pressure. Tracking the blood pressure feature could then provide a comparable indication of the progression of the disease.

To create a library of features, a signal associated with neuronal activity of a mammalian brain may be received using electrodes described herein. The patient may have a known disease state or be undergoing a disease treatment. Non-linear processing of the signal may be used to extract a signal feature. Following, the signal feature may be associated with the patient's disease state. Lastly, the signal feature and the disease state may be stored in a library of features, as further described below.

A feature set can be derived using any suitable algorithm, such as, for example, a genetic algorithm. Genetic algorithms are a form of evolutionary algorithm based on concepts of evolutionary biology, including inheritance, mutation, selection, and crossover. In application, genetic algorithms can be used to find exact or approximate solutions. Such algorithms are described in commonly-assigned U.S. patent application Ser. No. 12/541,272 titled "Development of Fully-Automated Classifier Builders for Neurodiagnostic Applications," which is incorporated herein by reference in its entirety Other embodiments will be apparent to those skilled in the art from consideration of the specification and practice of the devices and methods disclosed herein. It is intended that the specification and examples be considered as exemplary only, with a true scope being indicated by the following claims.

What is claimed is:

1. A method for monitoring or evaluating a neurologic state of a patient, comprising:
    collecting data related to brain electrical activity of the patient at a first location using at least one electrode;
    transferring the data related to brain electrical activity to a memory unit located at a second location that is different from the first location;
    providing a processor configured to classify the neurological state of the patient based on the data related to brain electrical activity and data stored in a database;
    receiving data related to non-electrical diagnostic information related to the neurological state of the patient based on at least one evaluation technique;
    updating the database to include the data related to brain electrical activity and the non-electrical diagnostic information related to the neurological state; and
    correlating the data related to brain electrical activity and the data related to non-electrical diagnostic information to allow development of one or more diagnostic and treatment algorithm.

2. The method of claim 1, further including repeating the method with at least one additional patient using the updated database to classify the neurological state of the additional patient.

3. The method of claim 1, further including repeating the method, wherein collecting data related to brain electrical activity is performed with two or more patients at at least two or more different locations.

4. The method of claim 1, further including, upon classifying the neurological state, notifying a predetermined person that a classification has been provided so that the predetermined person can evaluate the patient and provide information related to the neurological state of the patient based on at least one evaluation technique not including brain electrical activity data.

5. The method of claim 1, wherein the classification includes at least one of a psychiatric disorder, an organic neurological disorder, a structural neurological disorder, a metabolic disorder, an intoxicated state, and a normal state.

6. The method of claim 1, wherein the classification includes at least one of an ischemic brain state and a hemorrhagic state.

7. The method of claim 1, wherein the classification includes an abnormal intracranial pressure.

8. The method of claim 1, further including providing a treatment recommendation based on data stored in the database and the classification of the neurologic state of the patient.

9. A method for monitoring or evaluating a neurologic state of a patient, comprising:
    collecting data related to brain electrical activity of a patient at a first location using at least one electrode;
    transferring the data related to brain electrical activity to a memory unit located at a second location that is different from the first location;
    classifying, using a processor, the neurological state of the patient based on the data related to brain electrical activity and data stored in a first database;
    providing an assessment of the neurological state of the patient based on data related to non-electrical diagnostic information about the patient;
    correlating a result of the classification with the assessment based on the data related to non-electrical diagnostic information;
    updating the first database to include the data related to brain electrical activity; and
    updating a second database containing longitudinal data related to the patient's a neurologic state at multiple time points.

10. The method of claim 9, further including collecting data related to brain electrical activity of the patient at a later time; and
    comparing the data related to brain electrical activity of the patient at the later time to data stored in the second database to determine a change in the patient's neurologic state.

11. The method of claim 9, further including providing a treatment recommendation based on data stored in the database and the classification of the neurologic state of the patient.

12. The method of claim 11, further including evaluating the response of a patient to a treatment and providing a subsequent treatment recommendation based on data stored in the database, the classification of the neurologic state of the patient, and the patient's response to the treatment.

13. The method of claim 9, wherein providing a classification includes identifying at least one similarity between the brain electrical activity data of the patient and brain electrical activity data stored in the first database for at least one additional patient having a known neurological state and assigning the known neurological state to the patient.

14. The method of claim 13, wherein the at least one additional patient includes a group of patients.

* * * * *